United States Patent
Kostrzewa

(10) Patent No.: US 10,106,831 B2
(45) Date of Patent: Oct. 23, 2018

(54) MICROBE IDENTIFICATION BY MASS SPECTROMETRY AND INFRARED SPECTROMETRY

(71) Applicant: Bruker Daltonik GmbH, Bremen (DE)

(72) Inventor: Markus Kostrzewa, Lilienthal (DE)

( * ) Notice: Subject to any disclaimer, the term of this patent is extended or adjusted under 35 U.S.C. 154(b) by 0 days.

(21) Appl. No.: 15/038,890

(22) PCT Filed: Nov. 10, 2014

(86) PCT No.: PCT/EP2014/074118
§ 371 (c)(1),
(2) Date: May 24, 2016

(87) PCT Pub. No.: WO2015/090727
PCT Pub. Date: Jun. 25, 2015

(65) Prior Publication Data
US 2017/0051330 A1    Feb. 23, 2017

(30) Foreign Application Priority Data
Dec. 20, 2013   (DE) .................. 10 2013 022 016

(51) Int. Cl.
G01N 33/68     (2006.01)
C12Q 1/10      (2006.01)
C12Q 1/04      (2006.01)

(52) U.S. Cl.
CPC ............... *C12Q 1/10* (2013.01); *C12Q 1/04* (2013.01); *G01N 33/6848* (2013.01); *G01N 33/6851* (2013.01)

(58) Field of Classification Search
CPC .................... G01N 33/6848; G01N 21/00
See application file for complete search history.

(56) References Cited

U.S. PATENT DOCUMENTS 8,652,800 B2    2/2014  Walsh et al.
2008/0132418 A1  6/2008  Ismail et al.
(Continued)

FOREIGN PATENT DOCUMENTS

WO      2010129779 A1   11/2010
WO   WO2013093913 A1    6/2013

OTHER PUBLICATIONS

Stamm et al: "Yersinia enterocolitica in Diagnostic Fecal Samples from European Dogs and Cats:Identification by Fourier Transform Infrared Spectroscopy and Matrix-Assisted Laser Desorption Ionization-Time of Flight Mass Spectrometry", Journal of Clinical Microbiology, vol. 51, pp. 887-893, Jan. 2013.
(Continued)

*Primary Examiner* — Rosanne Kosson
(74) *Attorney, Agent, or Firm* — Benoit & Côté Inc.

(57) ABSTRACT

The invention relates to a method for identifying unknown microbes in a sample, wherein a mass spectrometric determination termination down to the taxonomic level of the genus or species is supplemented by a detailed determination of a lower taxonomic level or variety by means of infrared spectrometry, using restricted reference libraries of infrared spectra. These libraries can be genus-specific, containing only infrared spectra of microbes of one genus, or species-specific, containing only infrared spectra of microbes of one species. In so doing, a robust mass spectrometric identification of the species of unknown microbes is advantageously supplemented with a detailed analysis of the subspecies and varieties by means of infrared spectrometry, primarily in order to identify medically important varieties such as pathovars like EHEC and EPEC, and antibiotic-resistant microbes like MRSA.

20 Claims, 3 Drawing Sheets

(56) References Cited

U.S. PATENT DOCUMENTS

2010/0129857 A1    5/2010   Walsh et al.
2013/0325771 A1   12/2013   Paauw et al.

OTHER PUBLICATIONS

Wang Y et al: "Differentaiation in MALDI-Top MS and FTIR spectra between two closely related species *Acidovorax oryzae* and *Acidovorax citrulli*", BMC Microbiology, vol. 12, No. 1, 2012, p. 182, XP021115254, tables 2-4.

Lai S et al: "Whole-organism Fingerprinting of the Genus Carnobacterium using Fourier Transform Infrared Spectroscopy (FT-IR)", Systematic and Applied Microbiology, vol. 27, No. 2, 2004, pp. 186-191, XP004957575, figure 1.

Ullom J et al: "Discriminiation between bacterial spore types using time-of-flight mass spectormetry and matrix-free infrared laser desorption and ionization", Analytical Chemistry, vol. 73, No. 10, 2001, pp. 2331-2337, XP002296692, figure 3.

Martiny, Delphine et al., "Comparison of Microflex LT and Vitek MS Systems for Routine Identification of Bacteria by Matrix-Assisted Laser Desorption Ionization-Time of Flight Mass Spectormetry", Journal of Clinical Microbiology, 0095-1137/12, p. 1313-1325, (2012).

Dieckmann, Ralf et al., "Rapid Classification and Identification of Salmonellae at the Species and Subspecies Levels by Whole-Cell Matrix-Assisted Laser Desorption Ionization-Time of Flight Mass Spectrometry", Applied and Environmental Microbiology, p. 7767-7778, (Dec. 2008).

Rebuffo-Scheer, Cecilia et al., "Differentiation of Listeria monocytogenes Serovars by Using Artificial Neural Network Analysis of Fourier-Transformed Infrared Spectra", Applied and Environmental Microbiology, p. 1036-1040, (Feb. 2007).

Barbuddhe, Sukhadeo, "Rapid Identification and Typing of *Listeria* Species by Matrix-Assisted Laser Desorption Ionization-Time of Flight Mass Spectrometry", Applied and Environmental Microbiology, vol. 74, No. 17, p. 5402-5407, (Sep. 2008).

Naumann, Dieter, "Infrared Spectroscopy in Microbiology", Encyclopedia of Analytical Chemistry, pp. 102-131, (2000).

Wenning, Mareike et al., "Identification of microorganisms by FTIR spectroscopy: perspectives and limitations of the method", Appl Microbiol Biotechnol, 97:7111-7120, (2013).

Hrabak, Jaroslav et al., "Detection of NDM-1, VIM-1, KPC, OXA-48, and OXA-162 Carbapenemases by Matrix-Assisted Laser Desorption Ionization-Time of Flight Mass Spectrometry", Journal of Clinical Microbiology, vol. 50, No. 7, p. 2441-2443, (Jul. 2012).

Timmins, Éadoin M. et al., "Rapid Differentiation of Closely Related Candida Species and Strains by Pyrolysis-Mass Spectrometry and Fourier Transform-Infrared Spectroscopy", Journal of Clinical Microbiology, vol. 36, No. 2, p. 367-374, (Feb. 1998).

Kim, S. et al. "Differentiation of outer membrane proteins from *Salmonella enterica* serotypes using Fourier transform infrared spectroscopy and chemometrics", Letters in Applied Microbiology, vol. 42, p. 229-234, (2006).

MICROBE IDENTIFICATION BY MASS SPECTROMETRY AND INFRARED SPECTROMETRY

FIELD OF THE INVENTION

The invention relates to methods for identifying microorganisms in a sample by spectrometric means.

In the invention, a robust mass spectrometric identification of the species of unknown microbes is supplemented with a detailed analysis of the subspecies and varieties by means of infrared spectrometry, primarily in order to identify medically important varieties such as pathovars (for example EHEC and EPEC) and antibiotic-resistant microbes (for example MRSA). The detailed analysis by means of infrared spectrometry requires knowledge of the microbe species in order to use a species-specific and species-restricted database (library) of reference IR spectra, and especially in order to carry out species-specific, standardized culturing of the microbes. The mass spectrometric identification of the microbes is carried out by means of similarity comparisons between their mass spectra and reference spectra of microbes across all taxonomic domains in an extensive database (library). The detailed analysis of the subspecies and varieties, on the other hand, is performed using IR spectra, in essentially the usual way, via a mathematical-statistical classification analysis, here applied to a quantity of reference IR spectra of the subspecies and varieties of only a single species of microbe. This identification has at least two steps and is primarily of interest for medical diagnostics.

BACKGROUND OF THE INVENTION

The rapid, error-free identification of microorganisms plays a prominent role in clinical microbiology in particular, but also in food analysis, monitoring and control of biotechnological processes, and monitoring of rivers and lakes. Microorganisms, which are also referred to as germs and microbes below, are generally microscopic organisms, which include bacteria, unicellular fungi (e.g. yeasts), microscopic algae and protozoa.

Identifying a microorganism means classifying it in the taxonomic hierarchical scheme: domain, kingdom, phylum, class, order, family, genus, species, and subspecies. The identification of bacteria, however, can additionally encompass varieties, such as serotypes or pathovars.

The term serotype or serovar (short for serovariety) is used to describe varieties within subspecies of bacteria which can be differentiated with serological tests. They differ in respect of antigens on the surface of the cells, and are identified in conventional microbiology with the aid of specific antibodies. The taxonomic hierarchy for serotypes is as follows: genus>species>subspecies (subsp.)>serotype, for example with the extended binomial species name *Salmonella enterica* subsp. *enterica* serotype Typhi, short form *Salmonella* Typhi.

A pathovar (from the Greek pathos, meaning "suffering" or "disease") is a bacterial strain or group of strains with the same properties that is differentiated from other strains within the species or subspecies on the basis of its pathogenicity. Pathovars are designated by means of a ternary or quaternary extension to the binomial species name. The bacterium *Xanthomonas axonopodis*, for example, which can cause citrus canker, has various pathovars with different host specializations: *X. axonopodis* pv. citri is one of them. The abbreviation "pv." stands for "pathovar". The virulent strains of human pathogens also have pathovars, but in this case they are designated by an addition before the name. For example, the intestinal bacterium *Escherichia coli*, which is mostly completely harmless, has the highly dangerous pathovars enterohaemorrhagic *E. coli* (EHEC), enteropathogenic *E. coli* (EPEC), enterotoxigenic *E. coli* (ETEC), enteroinvasive *E. coli* (EIEC), enteroaggregative *E. coli* (EAEC) and diffusely adherent *E. coli* (DAEC). The pathovars, in turn, can contain different serotypes. EHEC has many known serotypes, with around 60 percent of all identified EHEC serotypes being O157, O103 and O26. Particularly dangerous is the serosubtype O157/H7.

In a broader sense, the identification of microbes can also encompass varieties which differ in other medically relevant properties, in particular their resistance to antibiotics (especially beta-lactam antibiotics and glycopeptide antibiotics), but also their toxin formation ("toxivars") or their receptiveness to the same or similar bacteriophages ("phagovars"). In general, the term "biovars" is used if a group of microbes of one species or subspecies have biological properties in common. One example of an antibiotic-resistant variety is MRSA: Methicillin-resistant *Staphylococcus aureus*.

The term "strain" describes a population that was grown from a single organism and is kept in a (often national) repository for microbial strains. An internationally standardized strain designation is added to the nomenclature chain, comprising genus, species, subspecies and variety. The individual organisms of a strain are genetically identical; different strains vary slightly in their genetic make-up.

Two spectrometric methods have recently become widely used in microbiological laboratories for the identification of microbes. One of these is mass spectrometry (MS), and the other is infrared spectrometry (IR). It must be noted here that, strangely enough, no research group so far uses the two methods in parallel, or indeed in combination. On closer examination, this can be explained by the fact that the research fields of these groups are different in most cases, as are the aims of the identifications.

It is always favorable to use mass spectrometry when microbes of a completely unknown species have to be identified quickly and easily, down to the taxonomic level of the species, with no prior knowledge whatsoever. In general, the method works very well as long as the microbes can be cultured on or in nutrient media. It is preferable to produce colonies on gelatinous nutrient media in Petri dishes. The method is very robust: the age and nutrition of the colony have practically no effect on the mass spectrometric identification; nor are the quantities, preparation methods or storage periods of the samples on the mass spectrometric sample supports of any great importance. This means that the method of sample propagation and preparation does not require any strict standardization. Moreover, only very little sample material is needed, so tiny colonies are sufficient. The peaks of the mass spectra indicate microbe proteins that are exceedingly common or easy to ionize; 60 to 85 percent of these peaks belong to the 40 to 60 different proteins making up the ribosomes. Since each ribosome occurs several thousand times in each cell, and since the masses of the ribosomal proteins for the different microbe species are all characteristically different from each other, the uniform incidence of these proteins makes them ideal for an identification. After successful cultivation, the method identifies the taxonomic species of the microbes under investigation in a matter of minutes by using automated computer programs to compare their mass spectra with the reference mass spectra of an extensive spectral library, which may contain thousands of reference mass spectra of microbes across all taxonomic domains. The method has a very high identification certainty. In only a few cases is it not possible to differentiate between two microbe species with certainty. On the other hand, it is rarely possible to identify subspecies or even varieties, and, according to current knowledge, this will scarcely change on the basis of the methods currently in use, which are optimized for sensitivity, speed and identification accuracy. The principal reason for this is that the varieties do not differ in respect of their ribosomal proteins.

With infrared spectrometry, in contrast, it is possible to identify subspecies and varieties such as serotypes and pathovars, in some cases even individual strains within a species, if a suitable library of reference spectra for the subspecies and varieties of this species is available. The compiling of this library, however, usually requires that species-specific culture, preparation and measuring specifications are accurately adhered to, which is quite different to the situation with mass spectrometry.

The IR spectra are based on thousands of vibrations of the functional groups and the polar bonds in the biological material; these in turn originate from all the components of the microbial cells such as DNA, RNA, proteins, internal structures, membranes, and cell walls, right through to energy stores. There are no unequivocal assignments of molecules to individual characteristics in the spectra, albeit certain spectral ranges can be preferably assigned to certain molecular species: the fatty acid range from 3050 to 2800 $cm^{-1}$ with vibrations of the $CH_2$ and $CH_3$ groups, the amide range from 1750 to 1500 $cm^{-1}$ with peptide bonds, the polysaccharide range from 1200 to 900 $cm^{-1}$. The range from 900 to 700 $cm^{-1}$ is called the "fingerprint range". It contains something from all the molecules and is very important for differentiating between the species.

The identifications depend on tiny differences in the IR spectra, which is why all method steps for identification via IR spectra are usually standardized, from the cultivation of the microbes with prescribed durations and temperatures on prescribed nutrient media through to the preparation and measurement of the samples. Oxygen content and moisture level above the nutrient medium must be controlled. Small deviations from the standardized method, such as a deviation in the culture period of more than half an hour or the culture temperature of more than one Kelvin, are enough to make the identification more difficult or falsify it.

In order to compile a library of reference IR spectra, microbes of a selected group are cultured and measured under standardized conditions. The spectra of this reference library are then subjected all together to a mathematical-statistical classification procedure. Several mathematical-statistical methods are used, such as ANN (artificial neural network analysis), PCA (principal component analysis), PLS-DA (partial least-square discriminant analysis), SVM (support vector machines), hierarchical cluster analyses or other classification techniques. After a learning and verification phase with the aid of the IR spectra from the library, the classification algorithms can then be applied to the infrared spectrum of the microbes of a sample, which were cultured in the same way. The algorithms provide the taxonomic classification, such as species, subspecies, serotype, pathovar and even strain. If, however, the microbe in the sample does not belong to the closely related group, the detailed IR analysis can provide totally incorrect results. As an example, the pathovar EHEC may be falsely indicated if the microbes are not *E. coli*, as assumed, but relatively harmless *Citrobacter*, for example.

These differences in handling and results mean that the fields of application for MS and IR are different. In clinical diagnostics, only mass spectrometry is used in practice, because unknown pathogens must be assumed across all taxonomic domains. The same applies to the monitoring of rivers and lakes and in all other areas where a fast identification of any type of microbes without any prior knowledge of the microbiological species is of paramount importance. The microbes here can belong to all the taxonomic domains of bacteria, archaea and eukaryotes, including unicellular algae or fungi, such as yeasts.

In contrast, if the aim is to detect sources of contamination and transmission routes of microbes in contaminated food or infected livestock, it is important to determine subspecies and varieties for a reliable identification of the infection sources. In this case, it can usually be assumed that the species of the microbes is known, at least after a single microbiological determination. Nowadays, therefore, IR spectrometry is used mainly where the species of the microbes is known, but it is important to accurately determine the subspecies and possibly the variety. If, for example, endemic *salmonella* poisoning occurs, and if it is suspected that the *salmonella* originate from an aquaculture of Thai shrimps, it is not sufficient to detect *salmonella* in the Thai shrimps. According to current taxonomy, there are two species of *salmonella*, one of which (*Salmonella enterica*) has five subspecies, but these have around 2600 different serovars as varieties between them. To come back to the shrimps, one then has to prove that the same *salmonella* variety is involved. The *salmonella* from a stool sample are therefore grown in a *salmonella*-specific culture broth, and IR spectrometry is used to examine the serotype of the selectively grown *salmonella*. This serotype must then be traced back to the Thai aquaculture.

Thus, infrared spectrometry is to be found mainly in food production, veterinary medicine and public health authorities, whereas clinical diagnostics is dominated by mass spectrometry.

Nowadays, the mass spectrometric identification method is also used around the world for medical diagnostics; in European and many other countries, methods and mass spectrometers from individual companies have already been clinically approved, as they meet the appropriate legal stipulations. Statutory approvals are being prepared in other countries. In the mass spectrometric method, the microbes are first cultured to form colonies. The nutrient medium for the culture is usually in an agar in a Petri dish, and by this method the cultivation of pure "isolates" in separate microbe colonies is achieved in hours or days, depending on the vigor of the microbes. It is not absolutely imperative to grow the microbes on agar, however. They can also be grown in liquids. If the colonies superimpose or mix, it is possible to obtain isolated colonies, again in the usual way, in a second cultivation. The tiny quantity of $10^4$ to $10^6$ microbes, hardly visible to the naked eye, which is transferred from a selected colony onto the mass spectrometric sample support by means of a small swab (preferably with a hygienically clean wooden toothpick), is then sprinkled with a strongly acidified solution of a conventional matrix substance (usually α-cyano-4-hydroxycinnamic acid, HCCA, or 2,5 di-hydroxybenzoic acid, DHB) for a subsequent ionization by matrix-assisted laser desorption (MALDI). The acid (usually formic acid or trifluoroacetic acid) attacks the cell walls, and the organic solvent (usually acetonitrile) of the matrix solution can penetrate into the microbial cells and cause their weakened cell walls to burst osmotically. The sample is then dried by evaporating the solvent, causing the dissolved matrix material to crystallize out. The soluble proteins of the microbes, and also other substances of the cell to a very small extent, are incorporated into the matrix crystals in the process.

The matrix crystals with the incorporated analyte molecules are bombarded with focused UV laser pulses in a mass spectrometer, thus generating ions of the analyte molecules in the vaporization plasmas. These ions can then be measured in the mass spectrometer, separated according to their mass. Simple time-of-flight mass spectrometers are commonly used for this purpose. The mass spectrum is the profile of the mass values of these analyte ions, which are very predominantly protein ions. The ions with the most useful information in terms of an identification have masses of between approximately 3,000 daltons and 15,000 daltons (1 dalton=1 atomic mass unit). In this method, the protein ions are very predominantly only singly charged (charge number z=1), which is why one can also simply talk about the mass m of the ions here, instead of always using the term "mass-to-charge ratio" m/z, as would otherwise actually be necessary in mass spectrometry.

Instead of simple time-of-flight mass spectrometers, it is also possible to use other types, such as time-of-flight mass spectrometers with orthogonal ion injection; and instead of the ionization by MALDI, it is certainly possible to use other types of ionization, such as electrospraying (ESI), although they provide more complicated mass spectra. A different ionization method for the generation of simple mass spectra is chemical ionization (CI), which can be used with laser-desorbed plasmas, for example.

The mass-separated profile of the soluble proteins, i.e. the mass spectrum, is very characteristic of the microbe species concerned because every species of microbe produces its own, genetically determined proteins, each having a characteristic mass. As has already been mentioned, around 60 to 85 percent of the proteins originate from the ribosomes. These are complexes of DNA and proteins which always have the same structure and which always contain between 40 and 60 different species-specific proteins in precisely the same number and composition. Each bacterial cell contains several thousand, and up to ten thousand, ribosomes; cells of eukaryotes contain several hundred thousand ribosomes. This means that not only the masses, but also the incidences of these soluble, more highly concentrated proteins are genetically predetermined; they do not depend on the nutritional conditions or the maturity of the colony, as do the lipoproteins, or the fatty acids which act as energy stores, for example. The protein profiles, especially those of the ribosomal proteins, are similarly characteristic of a microbe species as fingerprints are of an individual person. Reference libraries with reference mass spectra for thousands of microbes, which are legally approved for use in medical applications, are now available.

This mass spectrometric method of identification has proven to be extremely successful. The certainty of a correct identification is far greater than with the microbiological identification methods currently in use. In various studies it has been possible to prove that, with hundreds of different species of microbe, the identification certainty was far greater than 95 percent, and usually more than 98 percent. In cases of doubt, where there were deviations from current microbiological identification methods, genetic sequencing has confirmed that the mass spectrometric identification was correct in the vast majority of cases.

To identify the microbes, mass spectra from around 2,000 daltons up to high mass ranges of 20,000 daltons, for example, are measured, but it has been found that the mass signals in the lower mass range up to around 3,000 daltons can be evaluated less well because they can originate from substances whose presence is essentially random and variable, such as fatty acids, which are stored according to the nature of the nutrition. The best identification results are obtained by evaluating the mass signals in the mass range from around 3,000 to 15,000 daltons. The ultra-sensitive mass spectrometers now used for this purpose have only a low mass resolution, which means that the isotope groups, whose mass signals each differ by one dalton, cannot be resolved in this mass range. Only the envelopes of the isotope groups are measured.

This method of identifying microbes in principle requires a pure culture of microbes, a so-called "isolate", in order to obtain a mass spectrum that is free of superimposed signals of other microbes. It has, however, been found that mass spectra of mixtures of two microbe species can also be evaluated, and that both microbe species can be identified. The identification certainty suffers only slightly. If more than two microbe species are involved in the mass spectrum, or if these two microbe species are present in very different concentrations, the identification probability and identification certainty decrease considerably.

Microbe identification by IR spectrometry is also based on pure cultures of microbes on suitable nutrient media. Here, however, age- and nutrition-related differences in the microbes must be avoided by maintaining standard conditions, since all components of the cells contribute to the IR spectra in all wavelength ranges in each case. The microbes, which are grown on standardized agar under standardized conditions, are suspended in pure water and deposited on an IR-transparent support plate. Care must be taken to ensure that the microbes are deposited in a uniform layer. The layer is dried and the absorption of the microbes on the support plate is measured in an infrared spectrometer. A Fourier Transform spectrometer (FT-IR), which has a high resolving power, is normally used. The spectra typically measured range from 4000 $cm^{-1}$ to 500 $cm^{-1}$. Several hundred spectra are measured and summed at acquisition rates of 20 spectra per second in order to improve the signal-to-noise ratio.

In a slightly modified embodiment, the IR spectra can also be measured in reflected light, in which case they are prepared on a metallically reflective support, made of aluminum, for example. It is also possible to use Raman spectroscopy, which has the advantage that the microbe spectra can also be measured in liquids.

There are other fields, besides food inspection and veterinary medicine, where there is a need to classify microbes in as much detail as possible according to subspecies and variety, but in these other fields the species of the microbe is usually completely unknown initially. In medical diagnostics, for example, knowledge about the pathogenicity, toxicity, virulence, and particularly the antibiotic resistance of the microbes is extremely important. These properties can certainly be very different for different subspecies or varieties of one microbe species.

The subspecies, serotypes, pathovars and further variations of the microbes are determined from their microbiological characteristics, for example from their attachment behavior (serotypes), their toxicity, their pathogenicity (pathovars), their virulence, and also from their resistance or non-resistance to the different antibiotics. There is (as yet) no detailed knowledge about which of these variations can be differentiated spectrometrically.

In view of the foregoing, there is a need to identify microbes from a wide range of taxonomic classes, where the classification should also extend in particular to manifestations below the taxonomic level of the species, i.e. subspecies, pathovars, toxivars, serotypes, and especially resistance to antibiotics.

BRIEF DESCRIPTION OF THE INVENTION

The invention provides a method for identifying unknown microbes in a sample, wherein a mass spectrometric determination down to the taxonomic level of the genus or species is followed by a detailed determination of a lower taxonomic level or variety by means of infrared spectrometry, using restricted reference libraries of infrared spectra. These libraries can be either genus-specific, containing only infrared spectra of microbes of one genus, or species-specific, containing only infrared spectra of microbes of one species.

The invention is based on the finding that infrared spectroscopy can currently penetrate to lower levels of taxonomic classification (including the determination of varieties) than mass spectrometric identification is able to, but only if the reference infrared spectra used in the mathematical analysis belong only to a small group of closely related microbes, and in particular only if the infrared spectra were obtained in compliance with standardized specifications for the culture, preparation and measurement of the microbes of this group of related microbes. If reference IR spectra of all microbes across all taxonomic domains are brought together in a library and used for the classification, one cannot then expect that the resulting identification of bacteria in a sample will do much more than determine whether the bacteria are Gram-positive or Gram-negative, where applicable. The results improve if the reference library is limited to bacteria and, additionally, the microscopic distinguishing features of the bacteria are taken into account, and if each library of IR spectra that is created is restricted to either club-shaped (*corynebacteriaceae*), or spherical (cocci), or rod-shaped (bacilli) bacteria, or other morphologies. If, in a still further restriction, the reference library consists only of IR spectra of different pathovars of a single microbe subspecies, then it is often possible to unequivocally determine the pathogenic type of the microbes in a sample by means of infrared spectrometry, if the sample microbes do in fact belong to this subspecies. However, if the infrared spectrum of the microbes under investigation does not belong to the expected initial group after all, the method can lead to incorrect results, which, in the case of medical diagnostics, can be life-threatening. For optimal results, the specifications for the culture, preparation and measurement differ from microbe species to microbe species.

The invention provides methods, for example, whereby a mass spectrometric determination of the microbe species is followed by a detailed determination of the subspecies and/or the variety by means of infrared spectrometry, for which purpose a species-specific library of reference IR spectra is used. Once the microbe species is known, a decision can be taken as to whether a further detailing according to subspecies or variety is necessary, and can be carried out. For the classification according to subspecies or variety, a database of IR spectra restricted to this species and containing reference spectra of the different subspecies and varieties must be available. When the answer to the question of necessity and possibility is in the affirmative, an IR spectrum can be analyzed for subspecies or varieties. If required, the microbes can be cultured further in exact accordance with the standard specifications for this species, which are in the appropriate IR spectral database, and the microbes can be prepared for the subsequent acquisition of an IR spectrum. For optimum results, it may be necessary to apply an individual set of culture and preparation conditions for each microbe species which is optimal for the IR identification of the varieties. This set of conditions also forms the basis of the IR spectra, meaning that an individual IR reference database must be compiled for each microbe species.

The invention therefore involves an approach with at least two stages: first, the determination of the microbe species by means of the mass spectrometric method, then the determination of subspecies and variety, such as pathovar or serotype, by means of infrared spectrometry. If, as is known for some genera, mass spectrometry can only determine the genus with certainty, but not the species, IR spectrometry can be used to determine the species of the microbes on the basis of an appropriately compiled genus-specific library of IR spectra. A three-stage method may then become necessary to determine subspecies and variety.

In another method according to the invention, an infrared spectrum used for the detailed determination can be acquired before a mass spectrum used for the mass spectrometric determination is acquired, and at least parts of the same microbe material is used for both acquisitions, especially after a single culture.

To differentiate between subspecies and varieties, it can be favorable to use only specific parts of the microbial cells, for example the cell walls with the proteins located on their outside, for the IR spectra, since these proteins determine the serotype and usually also the pathovar. A precondition here is again a prior, certain identification of the species and the existence of an appropriate database for IR spectra from these parts of the microbial cells. The preparation of the cultured microbes can thus comprise their simple sedimentation onto a sample support, but also the destruction of the cells and the selection of those cell components which are more favorable than the complete microorganism for determining the variation. The components can be separated by centrifugation or filtration, especially by liquid gradient centrifugation, possibly also after derivatization, coagulation or other modifications.

This method of operation requires the existence of species-specific libraries of IR spectra of the microbial subspecies or even of the cell components of the microbial subspecies. This sounds like a vast undertaking which cannot be mastered. It is, however, general experience that in microbiological routine laboratories, only a small number of microbe species account for over 80 percent of the identifications which have to be done on a daily basis. Only three or four of these may require a more detailed classification; in addition, a few of the rarer microbe species may be interesting for a more detailed classification. While these microbe species of most urgent interest may differ from laboratory to laboratory, depending on the particular business focus, their relatively small number makes it possible to compile libraries of IR spectra which are suitable for these microbes. It has, furthermore, become apparent that an exchange of spectral libraries between different laboratories is possible if the strict standardization is adhered to.

Figure 2:
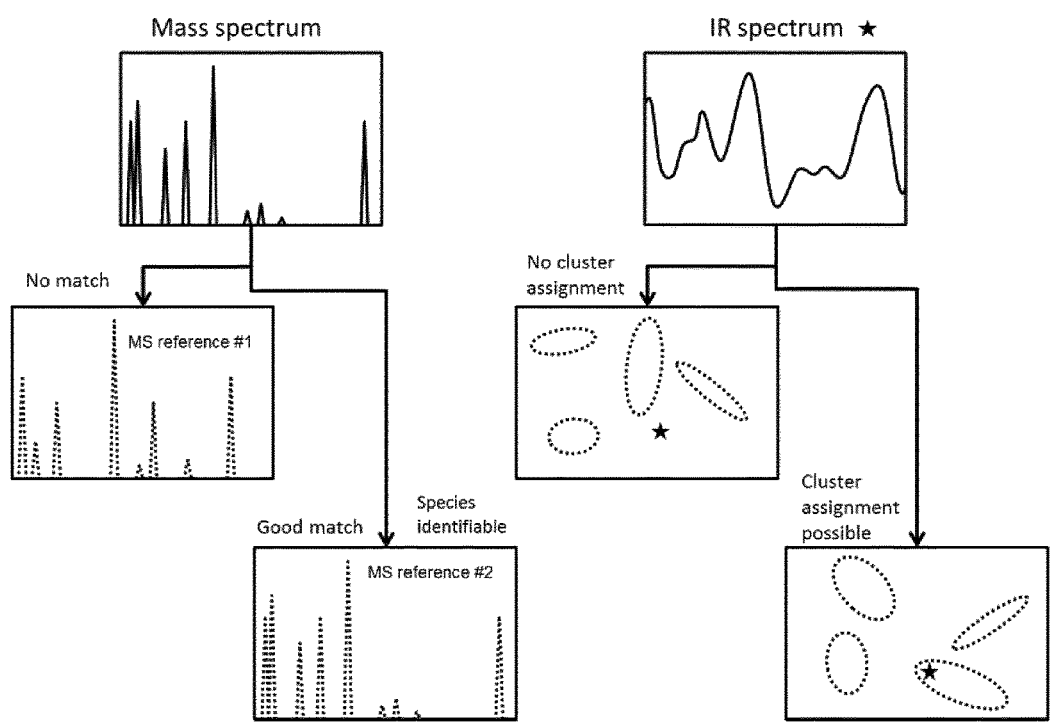

The left-hand side of FIG. 2 shows a simple and schematic embodiment for determining the species of a microorganism. A mass spectrum of components typical of the microorganism is acquired, and these components are represented by a particular mass signal pattern in the mass spectrum. The signal pattern is compared with patterns from a library of reference spectra, here MS reference #1 and #2. MS reference #1 does not show sufficient agreement with the measured signal pattern; in contrast, there is a good match between MS reference #2 and the measured signal pattern, so the species of the microorganism can be determined. The right-hand side of FIG. 2 illustrates a simple and schematic embodiment for determining the subspecies and variety by means of infrared absorption spectrometry. To this end, in a special embodiment, the microorganisms that have already been classified successfully by species using mass-spectrometric analysis are cultured, prepared and then measured by IR absorption spectrometry under specific, predetermined conditions. Characteristics of the infrared absorption spectrum (IR spectrum) thus obtained can then be elaborated and visualized, for example by applying a principal component analysis (PCA), within the species-specific reference IR spectra. The main components of the infrared absorption spectrum measured (represented in the diagram by stars ★) can then be entered on a "map", which also contains clusters of subspecies or varieties of the known species of the microorganism, i.e. locations where the parameters for specific subspecies or varieties are positioned after comparable culture, preparation and IR measurement. In a first example, the parameter ★ is outside all the clusters and is therefore not identifiable. In a second example, the parameter ★ can be assigned to a cluster and is thus determined to be a subspecies or variety.

Figure 3:
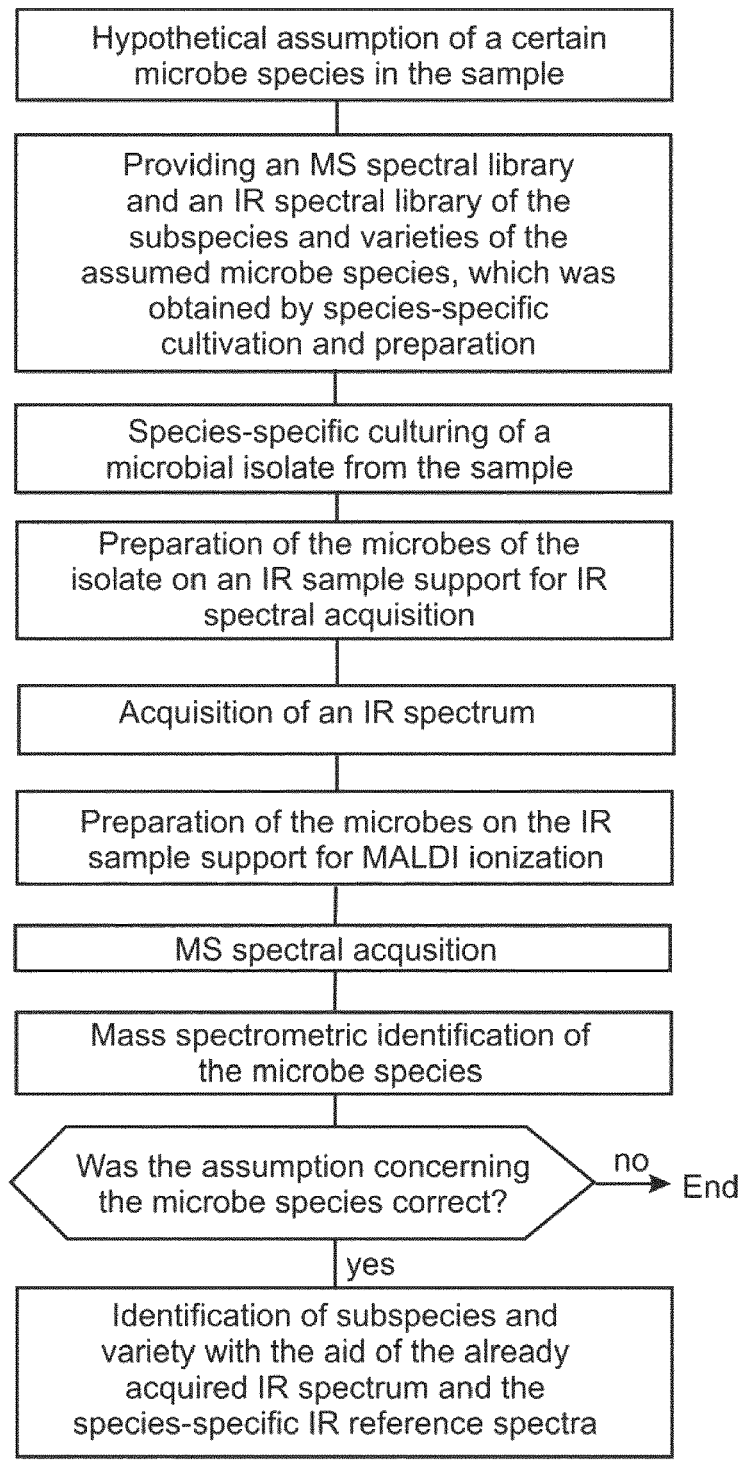

FIG. 3 shows an example of a flow chart for identifying subspecies and varieties of microbes according to a second embodiment. The method starts with a hypothetical assumption of a certain microbe species in the sample. Then, an MS spectral library and an IR spectral library of the subspecies and varieties of the assumed microbe species, which was obtained by species-specific cultivation and preparation, are provided. Then, a microbial isolate from the sample is cultured species-specifically. Then, the microbes of the isolate are prepared on an IR sample support for IR spectral acquisition. Then, an IR spectrum is (or IR spectra are) acquired. Then, the microbes are prepared on the IR sample support for MALDI ionization. Then, MS spectra are acquired. Then, mass spectrometric identification of the microbe species is performed. Then, a query is made of whether the assumption concerning the microbe species was correct. If no, the method ends here in this example. If yes, then subspecies and variety are identified with the aid of the already acquired IR spectrum and the species-specific IR reference spectra.

DETAILED DESCRIPTION

The mass spectrometric methods currently in use can usually identify only the species with certainty; in favorable cases the subspecies also; but in a few rare cases, only the genus of microbes. It should again be emphasized here that the invention is based on the finding that infrared spectrometry can currently penetrate to lower levels of taxonomic classification than mass spectrometric identification is able to. This only applies if the infrared spectra used in the mathematical classification analysis contain a small group of closely related microbes, for example of only one genus or only one species, or even one subspecies, and the microbes are preferably grown under standardized, genus-, species- or subspecies-specific conditions. If the reference library consists only of IR spectra of different pathovars and serovars of a single microbe species, then it is often possible to unequivocally determine the pathogenic type or serotype (or at least the pathovar or serovar group) of the microbes in a sample, provided that the sample microbes actually belong to this species. If the microbe spectrum does not belong to the species expected, an assignment is not possible.

In medical diagnostics, in particular, there are, however, cases where microbes from blood, nasal mucus, stool or urine are initially unknown to a large extent, but which must be characterized as precisely as possible down to the varieties such as biovars, serovars, phagovars, or pathovars, usually after determining the species. The term "pathovars" alone implies that not all varieties of the species are pathogenic, but in medical diagnostics it is mainly the pathogenicity which counts. Since this determination cannot usually be done by mass spectrometry alone, one of the methods according to the invention can be used in such cases.

The methods according to the invention for the taxonomic identification of microbes in a sample are essentially characterized by the fact that a mass-spectrometric determination of the species is supplemented by a determination of the subspecies and/or variety by means of infrared spectrometry. A species-specific library of reference IR spectra is used for the determination of subspecies and variety.

In a first embodiment of the method according to the invention, the mass spectrometric identification of the microbe species is followed by a reculture and preparation of the microbes for the purpose of determining the subspecies and variety. This reculture and preparation is performed according to precisely the same specifications under which the IR spectra of the species-specific IR library of reference spectra were obtained. The preparation of the microbes for the IR spectra may even comprise the selection and separation of individual cell components from which the IR spectra are acquired. For example, purified cell walls can be used to acquire the IR spectra. It is also possible to use any chosen fraction of the cell components obtained by gradient centrifugation. The cell components can also be derivatized in order to obtain informative IR spectra.

Figure 1:
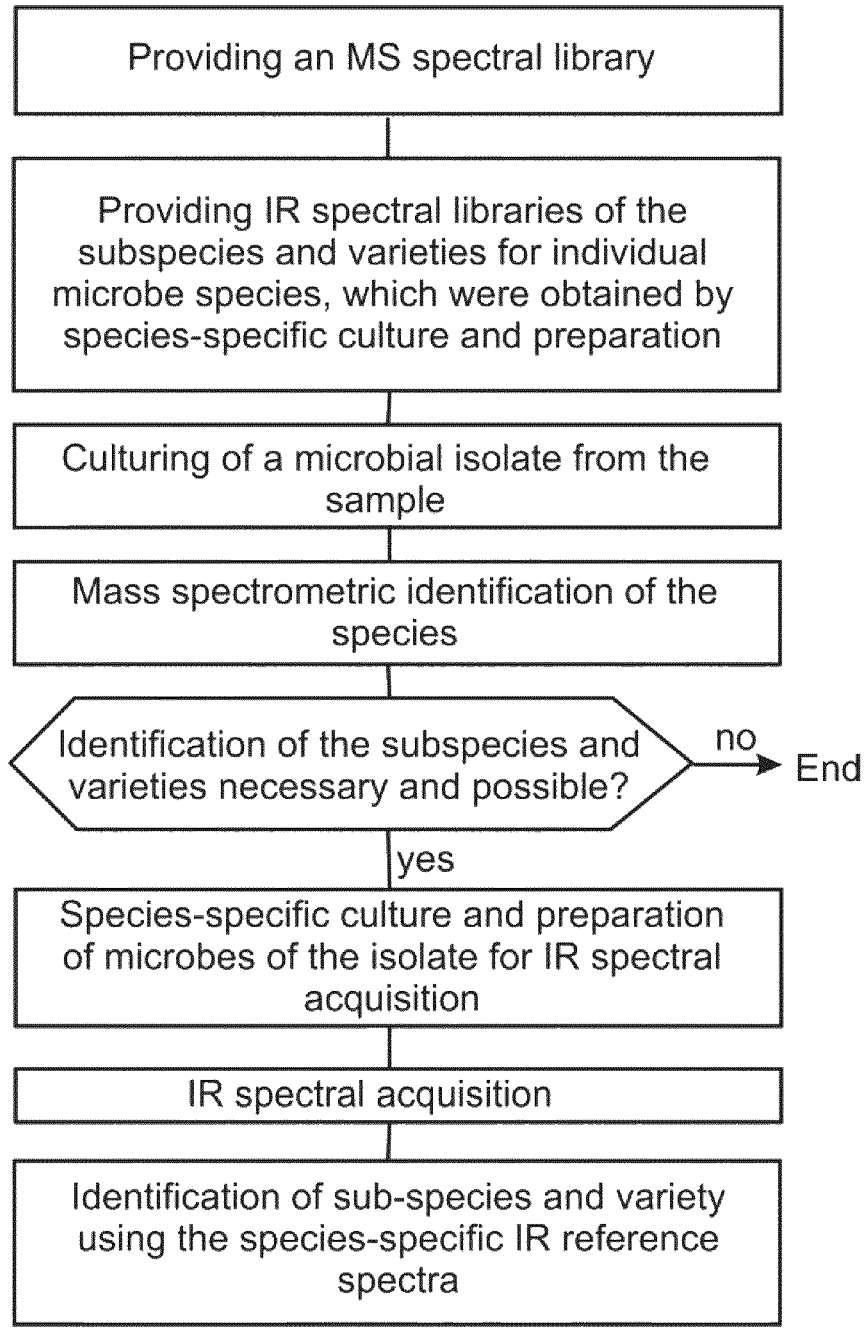
FIG. 1 shows an example of a flow chart for the identification of subspecies and varieties of microbes according to a first embodiment. The method starts with the provision of an MS spectral library. Then, IR spectral libraries of the subspecies and varieties for individual microbe species, which were obtained by species-specific culture and preparation, are provided. Then, a microbial isolate from the sample is cultured. Then, mass spectrometric identification of the species follows. Then, the query is made of whether identification of the sub-species and varieties is necessary and possible. If no, the method ends here in this example. If yes, species-specific culture and preparation of microbes of the isolate for IR spectral acquisition ensues. Then, IR spectra are acquired. Finally, sub-species and variety are identified using the species-specific IR reference spectra.

As can be seen in FIG. 1, this first embodiment of the method according to the invention for the determination of the species, subspecies and/or variety of unknown microbes in a sample comprises the steps
   a) provision of a library with reference mass spectra and libraries with reference IR spectra which were obtained specific to the species,
   b) culture of a microbial isolate from the sample,
   c) mass spectrometric determination of the species of the microbes,
   d) culture and preparation of microbes of the isolate according to the species-specific specifications under which microbes for the library of reference IR spectra for this species were obtained,
   e) acquisition of an infrared spectrum, f) determination of the subspecies and/or the variety by means of a mathematical-statistical classification method using the species-specific reference IR spectra.

The method can be terminated after Step c) if, after the mass spectrometric determination of the microbial species in Step c), it is ascertained that there is no need for a more detailed classification or that no database with reference IR spectra is available for such a classification.

Step d) of the culture and preparation of microbes according to the specifications for this species in the corresponding library of reference IR spectra already indicates that, for each species, there is a separate collection of reference spectra which were measured on microbes cultured according to standard methods, adapted precisely to this species. The standard methods can include stipulations relating to nutrient medium, duration and temperature of the culture, oxygen and moisture content above the nutrient medium, and also the type of sample preparation for the IR spectrometer, and finally even the weighting scheme for individual sections of the IR spectrum for the classification.

The preparation method can also require that certain cell components be selected if this is the only way to achieve a sufficiently good differentiation of varieties. Many serovars of bacteria, for example, are distinguished by the different types of lipopolysaccharides of the outer cell membrane (as surface antigens), and are then designated by O104:H4, for example, (this is the EHEC serovar of the most recent epidemic EHEC outbreak in 2011). The "O" here stands for "surface antigen". The precise differentiation of the lipopolysaccharides requires the separation and purification of the cell walls, but without dissolving the outer layer of the cell membrane.

This first embodiment can therefore comprise a preparation method whereby the cells of the microbes are carefully destroyed and the components of the cells are separated from each other, before an IR spectrum from one of the components is acquired. The cell digestion by destroying the cell walls must not be carried out in such a way that important components such as coat proteins and lipopolysaccharides are lost or destroyed. While a cell digest is usually carried out using strong acids (70 percent formic acid or trifluoroacetic acid) in order to dissolve all proteins as far as possible, it can be expedient here to carry out the cell digest with the enzyme lysozyme. The digested cells are then separated into individual cell components, preferably using gradient centrifugation, and only certain components, such as the cell walls, are used for the IR spectral measurement.

Whereas with the first embodiment, the mass spectrum is acquired first, and only then the IR spectrum, in a second embodiment this order is reversed. This second embodiment is preferable if one has an idea of what species of microbe is present in the sample. A species-specific culture is grown on the basis of this assumption, and an isolate from a colony is prepared on an IR spectrometric sample support. IR-transparent materials such as plates of zinc selenide or silicon have been used successfully as IR sample supports. After the acquisition of an IR spectrum, the microbe sample is then prepared for MALDI ionization, i.e. the microbes are digested and the contents of the microbial cells are prepared in matrix crystals. This can take place on the sample support for the IR measurement itself, for example on the silicon plate. The mass spectrometric acquisition leads to the identification of the microbe species, which confirms or disproves the assumption about the species. If the correct microbe species is present, the subspecies and, if applicable, the variety can now be determined from the IR spectrum already acquired. If such a determination were to take place without mass spectrometric confirmation of the assumed species, this could result in dangerous false positives or false negatives.

This second embodiment is particularly attractive because the IR spectra and the mass spectra can be obtained from the same microbes and, in special embodiments, on the same sample support plate also. FIG. 3 shows an example of a flow chart for this second embodiment.

This second embodiment is particularly suitable for use with enterobacteria, i.e. with *E. coli*. in particular. A trained specialist is already able to correctly identify the colony on the gelatinous nutrient medium in a Petri dish as *E. coli* with a probability of around 90 percent, so this procedure has a high probability of success. With *E. coli*, there is an urgent need to identify the pathotype, such as EHEC. If, however, a mass spectrometric confirmation for *E. coli* is not found, for example because it is *Citrobacter*, the evaluation of the IR spectrum can lead to diagnostically dangerous false results.

The exemplary methods mentioned above require that species- or preparation-specific libraries of IR spectra exist. These can actually be created by specialists in microbiological laboratories themselves, although this initially sounds like a vast undertaking which cannot be mastered. However, it has become apparent that, firstly, the strict standardization makes it possible to exchange spectral libraries between different laboratories; and, secondly, in microbiological routine laboratories, only four to six species of microbe account for over 80 percent of the identifications which have to be carried out on a daily basis. Only three or four of these may require a more detailed classification (example: *E. coli, salmonella, S. aureus*); in addition, a few of the rarer microbe species may be interesting for a more detailed classification. While these microbe species of most urgent interest may differ from laboratory to laboratory, depending on the particular business focus, they do allow individual laboratories to compile such libraries of IR spectra for these microbes over the course of time.

As has been briefly indicated above, in a few, but sometimes important, cases the mass spectrometric identification method cannot provide good and certain differentiation between two species (or even genera). For one microbe species, the mass spectrometric reference library usually contains between five and twenty reference spectra of different strains, these strains being selected in such a way that their reference spectra cover the variation in the mass spectra of this microbe species as broadly as possible. It can happen that the variations of the mass spectra of a certain species overlap with mass spectra of a different species, or even genus, in respect of their similarity. Such a case, which must be regarded as critical, is the problem of differentiating unequivocally between the *E. coli* species (which, apart from the above-described EHEC varieties, also has a variety which is a pathogen of the relatively harmless traveler's diarrhea) and the *Shigella genus* (four species; pathogens of shigellosis (bacillary dysentery), which requires medical treatment). The *E. coli* species has mass spectra with unusually great variation. They are thus occasionally extremely similar to the mass spectra of one or other of the four *Shigella* species (*Shigella boydii, Shigella dysentenae, Shigella flexneri* and *Shigella sonnei*), which can be easily distinguished from each other mass spectrometrically, and consequently a definite mass spectrometric identification is often not possible.

It should be mentioned at this point that the phylogenetic similarities lead some molecular biologists to believe that the four *Shigella* species do not form a distinct genus, but actually represent four subspecies of *E. coli*. Whether such a reclassification takes place in the future or not, the different therapeutic requirements mean that the problem of identifying this subspecies will remain.

A special embodiment of the method according to the invention described above provides assistance here, but in this case an IR reference library is used which contains microbes of the *Shigella* genus and the *E. coli* species. If the mass spectrometric identification of *Shigella* or *E. coli* is completely unequivocal, the procedure is successfully concluded. If it is not unequivocal, however, the IR spectrometric reference library is used which comprises the genus *Shigella* and the species *E. coli*, and it is preferable to culture the microbes according to the specification which was used to culture the microbes for the reference spectra of this IR spectrometric reference library. The IR spectra then allow a reliable determination of the species present. A small number of similar cases of this type require IR spectrometry for the final determination of the species, and for this, databases with reference IR spectra of all the species that cannot be differentiated by mass spectrometry are required.

To determine the subspecies and varieties of this species, a third step of the analysis may then be necessary, with special reference IR spectra for this species or with a special evaluation algorithm for the reference spectra of the genus, which are selected so as to be specific to the species. A definite identification of *E. coli* can thus be followed by a determination of the variety. *E. coli* is part of the normal intestinal flora and is harmless as such, but there are many pathogenic varieties. Apart from the already mentioned EHEC, which was first described in 1977 and comprises various serovars such as serovar O157, serovar O103 and serovar O26, there are further pathogenic *E. coli*: enteropathogenic *E. coli* (EPEC), enterotoxigenic *E. coli* (ETEC), enteroinvasive *E. coli* (EIEC), enteroaggregative *E. coli* (EAEC) and diffusely adherent *E. coli* (DAEC). Here too, it can be expedient to apply the fundamental method of destroying the microbial cells and separating the cell components from each other before acquiring an IR spectrum from one of the components. Only certain components, such as the cell walls, are used for the IR spectral measurement.

Of particular interest for any therapy is the resistance of a microbe to certain antibiotics, which still has to be determined with laborious analytical methods. It is possible that refined methods of IR spectral measurement will also enable specific resistance types to be determined. It is also to be expected that serovar types can correlate with resistances to antibiotics.

It is possible that the method according to the invention allows different types of resistance to antibiotics to be detected directly with IR spectrometry, possibly with only certain fractions of the microbes being used for the spectral measurement. These fractions can, for example, be obtained in essentially the known way after the cell walls have been destroyed by centrifugation, especially by density gradient centrifugation. Where applicable, components of the microbes can also be prepared by derivatization, coagulation or other biochemical modifications in such a way that the microbes with different resistances can be differentiated from each other by means of their IR spectra.

The invention has been described with reference to a number of different embodiments thereof. It will be understood, however, that various aspects or details of the invention may be changed, or various aspects or details of different embodiments may be arbitrarily combined, if practicable, without departing from the technical teaching of the invention. Generally, the foregoing description is for the purpose of illustration only, and not for the purpose of limiting the invention which is defined solely by the appended claims.

The invention claimed is:

1. A method for the identification of unknown microbes in a sample, wherein a mass spectrometric determination down to a species level is supplemented by a detailed determination of a subspecies or variety by means of infrared spectrometry, where a library of reference IR spectra specific to the species is used for the detailed determination of the subspecies or variety, wherein an infrared spectrum used for the detailed determination is acquired before a mass spectrum used for the mass spectrometric determination is acquired, and at least some of the same microbe material is used for both acquisitions, the method comprising the steps of:

making a hypothetical assumption that a certain microbe species is present in the sample,
   providing a library with reference mass spectra and a species-specific library with reference IR spectra for said certain microbe species,
   culturing and preparing a microbe isolate from the sample on an IR sample support plate using the same conditions under which microbes were cultured and prepared for said species-specific library of reference IR spectra,
   acquiring an IR spectrum of the cultured and prepared microbes of the isolate,
   preparing the microbes of the isolate for one of MALDI ionization, electrospray ionization, and chemical ionization,
   acquiring a mass spectrum and determining the microbe species of the isolate, and,
   if the hypothetical assumption about the microbe species has been confirmed, determining said subspecies or variety with a mathematical-statistical classification of the acquired IR spectrum using the reference IR spectra of the species-specific library of reference IR spectra.

2. The method according to claim 1, wherein the mass spectrometric determination of the microbe species is carried out by means of similarity comparisons between its mass spectra and reference mass spectra of microbes across all taxonomic domains in the corresponding library.

3. The method according to claim 1, wherein the culturing and preparing conditions include stipulations relating to nutrient medium, duration, temperature of the culture, oxygen and moisture content above the nutrient medium, type of sample preparation for an IR spectrometer, and a weighting scheme for individual sections of the IR spectrum for the detailed determination.

4. A The method according to claim 1, wherein individual sets of culture and preparation conditions for each microbe species, which are optimal for the IR determination of the associated subspecies or variety and have been compiled in individual IR reference libraries for each microbe species, are used for the detailed determination.

5. The method according to claim 1, wherein at least some of the same microbe material is used for both acquisitions after a single culture.

6. A method for the identification of unknown microbes in a sample, wherein a mass spectrometric determination down to a species level is supplemented by a detailed determination of a subspecies or variety by means of infrared spectrometry, where a library of reference IR spectra specific to the species is used for the detailed determination of the subspecies or variety, the method comprising the steps of:

providing a library with reference mass spectra and species-specific libraries with reference IR spectra, culturing a microbial isolate from the sample, acquiring a mass spectrum and performing said mass spectrometric determination of the species of microbe of the isolate, selecting one of said species-specific libraries of reference IR spectra in accordance with the mass spectrometric determination, culturing and preparing microbes of the isolate using the same conditions under which microbes were cultured and prepared for the reference IR spectra of said selected one of said species-specific libraries, acquiring an infrared spectrum of the cultured and prepared microbes of the isolate, and determining said subspecies or variety with a mathematical-statistical classification method, using the reference IR spectra of said selected one of said species-specific libraries, wherein the preparation of the microbes for the detailed determination comprises the selection and isolation of individual cell components, from which the IR spectra are then acquired.

7. The method according to claim 6, wherein said cell components comprise purified cell walls.

8. The method according to claim 6, wherein said cell components comprise a fraction of cell components obtained by gradient centrifugation.

9. The method according to claim 6, wherein said cell components are separated by one of centrifugation and filtration.

10. The method according to claim 6 wherein the mass spectrometric determination of the microbe species is carried out by means of similarity comparisons between its mass spectra and reference spectra of microbes across all taxonomic domains in the corresponding library.

11. The method according to claim 6, wherein individual sets of culture and preparation conditions for each microbe species, which are optimal for the IR determination of the microbe's subspecies or variety and which have been compiled in individual IR reference libraries for each microbe species, are used for the detailed determination.

12. The method according to claim 1, wherein the IR sample support plate comprises an IR transparent material.

13. The method according to claim 1, wherein preparing the microbes of the isolate for MALDI ionization comprises preparing the microbes of the isolate on said IR sample support plate.

14. A method for the identification of unknown microbes in a sample, wherein an uncertain mass spectrometric determination down to a genus or species level, is followed by a detailed determination of a true species by means of infrared spectrometry using a library of reference IR spectra containing solely infrared spectra of microbes of genera and species that cannot be differentiated mass spectrometrically with certainty, the method comprising the steps of:

providing a library with reference mass spectra and mixed genus-specific or species-specific libraries with reference IR spectra, culturing a microbial isolate from the sample, acquiring a mass spectrum and performing said mass spectrometric determination of a genus or species of microbe of the isolate which renders an uncertain result, selecting one of said mixed genus-specific or species-specific libraries of reference IR spectra, culturing and preparing microbes of the isolate using the same conditions under which microbes were cultured and prepared for the reference IR spectra of said selected one of said mixed genus-specific or species-specific libraries, acquiring an infrared spectrum of the cultured and prepared microbes of the isolate, and determining said true species with a mathematical-statistical classification method, using the reference IR spectra of said selected one of said mixed genus-specific or species-specific libraries.

15. The method according to claim 12, wherein preparing the microbes of the isolate for MALDI ionization comprises preparing the microbes of the isolate on said IR sample support plate.

16. The method according to claim 14, wherein the mass spectrometric determination renders an uncertain result of a species of the genus *Shigella* or the species *Escherichia coli* and wherein a mixed library of reference IR spectra containing solely infrared spectra of microbes of the genus *Shigella* and the species *Escherichia coli* is selected.

17. The method according to claim 14, wherein the mass spectrometric determination of the microbe species is carried out by means of similarity comparisons between its mass spectra and reference spectra of microbes across all taxonomic domains in the corresponding library.

18. The method according to claim 6, wherein the culturing and preparation conditions include stipulations relating to nutrient medium, duration, temperature of the culture, oxygen and moisture content above the nutrient medium, type of sample preparation for an IR spectrometer, and a weighting scheme for individual sections of the IR spectrum for the detailed determination.

19. The method according to claim 6, further comprising:

determining the genus of each unknown microbe in the cultured isolate from the sample by mass spectrometry, wherein the method is a three-stage method, wherein a mass spectrometric determination of the genus or genera of the microbes of the isolate is supplemented by detailed determinations of the species as well as subspecies or variety each using infrared spectrometry.

20. The method according to claim 14, wherein the culturing and preparing conditions include stipulations relating to nutrient medium, duration, temperature of the culture, oxygen and moisture content above the nutrient medium, type of sample preparation for an IR spectrometer, and a weighting scheme for individual sections of the IR spectrum for the detailed determination.

* * * * *